(12) United States Patent
Kahlert et al.

(10) Patent No.: US 10,813,696 B2
(45) Date of Patent: Oct. 27, 2020

(54) APPARATUS, METHOD AND COMPUTER PROGRAM FOR APPLYING ENERGY TO AN OBJECT

(75) Inventors: Joachim Kahlert, Aachen (DE); Michael Perkuhn, Eindhoven (NL); Josef Lauter, Geilenkirchen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2285 days.

(21) Appl. No.: 12/515,842

(22) PCT Filed: Nov. 27, 2007

(86) PCT No.: PCT/IB2007/054804
§ 371 (c)(1),
(2), (4) Date: May 21, 2009

(87) PCT Pub. No.: WO2008/065609
PCT Pub. Date: Jun. 5, 2008

(65) Prior Publication Data
US 2010/0063492 A1 Mar. 11, 2010

(30) Foreign Application Priority Data
Nov. 28, 2006 (EP) .................................. 06124884

(51) Int. Cl.
*A61B 18/24* (2006.01)
*A61B 18/00* (2006.01)
*A61B 18/22* (2006.01)
*A61B 18/14* (2006.01)
*A61B 17/00* (2006.01)

(52) U.S. Cl.
CPC .... *A61B 18/24* (2013.01); *A61B 2017/00026* (2013.01); *A61B 2017/00084* (2013.01); *A61B 2018/00214* (2013.01); *A61B 2018/00267* (2013.01); *A61B 2018/00839* (2013.01);
(Continued)

(58) Field of Classification Search
CPC .......... A61B 18/24; A61B 2018/00839; A61B 2018/00898; A61B 2018/00214; A61B 2018/2261; A61B 2017/0084; A61B 2017/0026; A61B 2017/00267
USPC .............. 606/2–19, 27–28, 31–33, 39–41, 1; 607/88–94, 115–116, 122; 128/898
See application file for complete search history.

(56) References Cited

U.S. PATENT DOCUMENTS 6,117,131 A 9/2000 Taylor
6,464,693 B1 10/2002 Andrews et al.
(Continued)

FOREIGN PATENT DOCUMENTS

DE 4038520 A1 6/1991
JP H10509338 A 9/1998
WO 0122897 A1 4/2001

OTHER PUBLICATIONS

Razavi et al: "Cardiac Catheterisation Guided by MRI in Children and Adults With Congenital Heart Disease"; The Lancet, vol. 362, Issue 9399, pp. 1877-1882, Dec. 6, 2003.
(Continued)

*Primary Examiner* — Boniface N Nganga

(57) ABSTRACT

An apparatus for applying energy to an object includes an arrangement of energy emitting elements for outputting energy to the object. At least some of the energy emitting elements are configured to emit energy to the object independently from each other.

35 Claims, 5 Drawing Sheets

(52) U.S. Cl.
CPC ............... *A61B 2018/00898* (2013.01); *A61B 2018/2261* (2013.01)

(56) References Cited

U.S. PATENT DOCUMENTS

| | | |
|---|---|---|
| 6,656,174 B1 | 12/2003 | Hegde et al. |
| 6,939,349 B2 | 9/2005 | Fleischman et al. |
| 7,052,492 B2 | 5/2006 | Swanson et al. |
| 7,474,909 B2 | 1/2009 | Phan et al. |
| 7,740,629 B2 | 6/2010 | Anderson et al. |
| 8,801,707 B2 | 8/2014 | Francischelli et al. |
| 2003/0078494 A1* | 4/2003 | Panescu et al. ............ 600/424 |
| 2003/0093072 A1 | 5/2003 | Friedman |
| 2003/0212394 A1* | 11/2003 | Pearson et al. ............ 606/41 |
| 2004/0186468 A1 | 9/2004 | Edwards et al. |
| 2005/0033285 A1 | 2/2005 | Swanson et al. |
| 2005/0119647 A1* | 6/2005 | He et al. ............ 606/41 |
| 2006/0009690 A1 | 1/2006 | Fuimaono et al. |
| 2006/0095022 A1* | 5/2006 | Moll et al. ............ 606/1 |
| 2007/0049924 A1* | 3/2007 | Rahn ............ A61B 18/1492 606/41 |
| 2008/0004534 A1* | 1/2008 | Gelbart ............ A61B 5/028 600/508 |

OTHER PUBLICATIONS

Ector et al: "Cardiac Three-Dimensional Magnetic Resonance Imaging and Fluoroscopy Merging: A New Approach for Electroanatomic Mapping to Assist Catheter Ablation"; Circulation 2005, vol. 112, pp. 3769-3776, Originally Published Online Dec. 5, 2005.

Schmitt et al: "Clinical Experience With a Novel Multielectrode Basket Catheter in Right Atrial Tachycardias"; Circulation 1999, vol. 99, pp. 2414-2422.

* cited by examiner

APPARATUS, METHOD AND COMPUTER PROGRAM FOR APPLYING ENERGY TO AN OBJECT

FIELD OF THE INVENTION

The invention relates to an apparatus, a method and a computer program for applying energy to an object.

BACKGROUND OF THE INVENTION

An apparatus for applying energy to an object is, for example, known in the field of ablation procedures in a heart. During ablation an ablation catheter is located within the heart and couples energy at certain locations on a surface of the heart into the heart tissue in order to denaturize parts of the heart tissue by heating. The ablation is, for example, performed in order to electrically isolate pulmonary veins to abort chaotic excitation that is mainly caused by electrical foci in the pulmonary veins.

The U.S. Pat. No. 7,052,492 discloses an ablation catheter having a plurality of electrodes to apply electrical energy to the heart. These electrodes can contact different locations on a surface of the heart to couple electrical energy at these locations into the heart. But this known ablation catheter is not able to differently act at different contact locations. This different activity is, for example, desirable because the heart or another object, to which energy should be applied, has often different properties at different locations, and a user, for example a physician, often wants to treat different parts of the heart or other objects differently.

SUMMARY OF THE INVENTION

It is therefore an object of the present invention to provide an apparatus, a method and a computer program for applying energy to an object, which allows acting on different parts of an object differently.

In a first aspect of the present invention an apparatus for applying energy to an object is presented, wherein the apparatus comprises an arrangement of energy emitting elements for outputting energy to the object, wherein at least some of the energy emitting elements are adapted for emitting energy to the object independently from each other.

The invention is based on the idea that, since at least some of the energy emitting elements are adapted for emitting energy to the object independently from each other, different amounts of energy can be applied to different parts of the object, i.e. the invention allows to differently act on different parts of the object. The invention allows, for example, that only certain energy emitting elements apply energy to the object, and/or that different energy emitting elements apply different amounts of energy to the object. Thus, the amount of energy required at a location, at which a certain energy emitting element is located, can be applied to the object at this location.

The object is, for example, a technical object, like a pipeline whose surface, in particular whose inner surface has to be treated, or an organ of a patient.

It is preferred that the arrangement of energy emitting elements comprises an abutting surface during applying energy to the object, wherein the energy emitting elements are located on the abutting surface at different locations and wherein the abutting surface can be abutted against an object surface. Since the abutting surface can abut against the object surface and since the energy emitting elements are located at different locations on the abutting surface, this arrangement of the energy emitting elements further improves the ability to apply different amounts of energy to different parts of the object.

The abutting surface is preferentially elastic for adapting to the object surface. This allows conforming the abutting surface to the object surface for minimizing the distance between the energy emitting elements and the object surface, in particular for contacting the object surface by the energy emitting elements (zero distance), during applying energy to the object. Furthermore, the elastic surface is preferentially capable of following a movement of the object such that the distance between the energy emitting elements and the object surface remains constant during applying energy and/or such that the energy emitting elements continuously contact the object surface during applying energy.

In a preferred embodiment, the arrangement of energy emitting elements is changeable between a first condition, in which the arrangement of energy emitting elements is formed as an abutting surface, and a second condition, in which the arrangement of energy emitting elements takes less space than in the first condition. This allows the arrangement of energy emitting elements to be introduced into the inside of the object, wherein the dimensions of the inside of the object are too small for introducing the arrangement of energy emitting elements in the first condition. This means, for introducing the arrangement of energy emitting elements, the arrangement of energy emitting elements comprises the second condition, and after introduction, within the object, the arrangement of energy emitting elements can be changed to the first condition, in which the abutting surface is formed.

It is preferred that the arrangement of energy emitting elements is unfoldable to the first condition and foldable to the second condition. This allows providing an arrangement of energy emitting elements, which is changeable between the first condition and the second condition in an uncomplicated way. Such an arrangement of energy emitting elements comprises, for example, a foldable basket form or a balloon, which can be filled with a liquid for changing to the first condition, wherein the liquid can be let out of the balloon for changing to the second condition.

The apparatus for applying energy to an object preferentially comprises a guiding element coupled to the arrangement of the energy emitting elements, wherein a location of the arrangement distant to the guiding element comprises an energy emitting element. This allows applying energy to a certain application location on the object by guiding the location of the arrangement distant to the guiding element to this application location, i.e., for example, without the need to change the arrangement of energy emitting elements to the first condition, in which the abutting surface abuts against the object surface. For instance, if the apparatus for applying energy to an object is an ablation catheter, the arrangement of energy emitting elements of the ablation catheter can comprise a basket, which is unfoldable to change to the first condition, in which the abutting surface abuts preferentially against an inner surface of a heart. On the distant tip of the basket an energy emitting element can be located for applying energy to a location of the heart, even if the arrangement of energy emitting elements is in its second condition, i.e. even if the basket is folded together.

The energy emitting elements can, for example, be electrodes. But, it is preferred that the energy emitting elements are adapted for outputting light energy. This allows, for example, using the apparatus for applying energy to an object together with a magnetic resonance imaging system. The energy emitting elements comprise preferentially diffusers or micro lenses for applying the light energy to a larger area of the object and for reducing the intensity of the energy applied to the object.

The arrangement of energy emitting elements preferentially further comprises sensing elements for sensing the object. The sensing elements are preferentially temperature sensors, electrical sensors, for example, for sensing electrical potentials of the object surface, pressure sensors or spectroscopic sensors for sensing light reflected from the object surface. The sensing elements are preferentially adapted for sensing the object surface. The sensing elements are preferentially connected to a property determination unit for determining properties of the object, in particular of the object surface, from sensing values obtained from the sensing elements. It is preferred that the sensing elements and the energy emitting elements are not both electrical elements, in order to be able to apply energy and sense the object simultaneously. If both kinds of elements are electrical elements, they would generally influence each other. For example, if the sensing elements are used together with energy emitting elements, which are adapted for emitting light energy, the application of energy and a sensing using electrical sensing elements can be performed simultaneously, because, in this case, the energy emitting elements and the sensing elements do not influence each other.

It is further preferred that the apparatus for applying energy to an object further comprises a control unit for controlling application of energy by the energy emitting elements, wherein the sensing elements are adapted for providing sensing values to the control unit, wherein the control unit is adapted for noticing, whether the sensing values are outside of a given range of operation. This allows a safety control of the application of energy to the object. If, for example, the application of energy modifies the properties of the object, for instance, the temperature or the electrical potential, this is sensed by the sensing elements and if the modification of the properties of the object, i.e. the sensing values, is not within a given range of operation, the application of energy is reduced, i.e. diminished or stopped. The given range of operation depends on the object, to which the energy is applied. For instance, if the object is a human organ, like the heart, the temperature of the object should not be above 80° C. respectively a user defined limit, i.e. the range of operation is, for example, about 37° C. to 80° C. If the control unit has noticed that the sensing values are out of range of operation, the control unit provides preferentially an alarm signal, preferentially an optical and/or acoustical alarm signal, and/or reduces the energy applied to the object.

It is further preferred that the object is a heart, wherein the arrangement is adapted for introducing into the heart for ablation. This adaptation for introducing into heart includes preferentially the use of bio-compatible materials for contacting the heart or another part of the patient, i.e. the parts of the apparatus for applying energy to an object, which can come into contact with the patient during a ablation procedure are made of or covered by bio-compatible material, i.e. material, which does not negatively influence the patient.

In an embodiment, the apparatus for applying energy to an object is provided with a model of the object and with a given path on the model of the object, wherein the apparatus comprises a registration unit for registering the model of the object with the abutting surface, wherein the arrangement is adapted such that the energy emitting elements of the registered abutting surface, which are arranged along the path, i.e. which are arranged substantially along the path, apply energy to the object. That is, energy emitting elements, which are located on the path or close to the path, emit energy, in order to apply energy substantially along the given path. This path can, for example, be a linear or a closed path. This allows applying energy to the object along a given path.

The path can be given by a user, which provides a path on the model, for example, by using a graphical user interface, which shows the model of the object and which provides means for drawing the path on the model. Alternatively or in addition, a path can be automatically determined by a path determination unit. The path determination unit receives the model of the object and sensing values of the sensing elements for determining the properties of the object, or properties of the object from a property determination unit, which has determined properties of the object by using the sensing values. The path determination unit determines a path from the received properties of the object depending on the desired treatment of the object. For example, if the object is a heart and the path has to enclose the ostium of a pulmonary vein, which can be determined from the sensing values, for example, from an electrical potential image of the heart generated by using the sensing electrodes, the path is determined such that it encloses, with a given distance to the edge of the ostium, the ostium of the pulmonary vein. The given distance can be predetermined by a user like a physician. The determined path can be shown on the graphical user interface, which can comprise means, for example, drag-and-drop means, for modifying the determined path.

The apparatus for applying energy to an object can also be adapted such that energy can be applied to the object along a given path formed by a group of energy emitting elements, which are, for example, aligned along an open or closed line. The energy emitting elements along the path can be predetermined, for example, by a user like a physician. This path has not to be necessarily predetermined on a model of the object. This path can also be given directly on the arrangement of energy emitting elements.

The model can be provided by imaging the object by an imaging system, like a computed tomography system or a magneto-resonance-imaging system. Furthermore, known reconstruction, segmentation and surface rendering methods can be used to generate a model of the object. It is preferred that a surface model of the object is the model. It is further preferred that a three-dimensional surface model of the object is provided to the apparatus for applying energy to an object. The model can also be provided by using sensing elements of the apparatus for applying energy to an object. These sensing elements be adapted for sensing the surface of the object and the resulting sensing values can be used for generating a model of the object surface, in particular, for generating a three-dimensional model of the object surface. For example, the sensing elements can sense the electrical potential of the object surface, and these electrical potential values can be used to generate a model of the object, in particular a three-dimensional surface model of the object.

It is further preferred that the apparatus for applying energy to an object is provided with a model of the abutting surface, wherein the apparatus comprises an imaging device for generating an image of the object and of the abutting surface, wherein the registration unit is adapted for registering the model of the object with the abutting surface by registering the model of the object and the model of the abutting surface with the generated image. This allows a particularly reliable registration.

The imaging device is preferentially a fluoroscopy device which generates X-ray projection images of the object and of the abutting surface. The model of the abutting surface shows preferentially at least the position and the dimensions of the energy emitting elements, and can, for example, be shown on a monitor located on the model of the object. The registration of the preferentially three-dimensional model of the object and of the preferentially three-model of the abutting surface uses preferentially the projection images and is preferentially performed by known 2D-3D-registration techniques. These 2D-3D-registration techniques use generally elements, which can easily be identified in both, the 2D representation and the 3D representation. These elements are, for example, bones, if the object is a patient or a part of patient, or contrast agents, which can be used in patients, but also in technical objects. These known 2D-3D-registration techniques are, for example, disclosed in Circulation 2005, 112:3769-3776 and Lancet 2003, 362:1877-1882.

In a further aspect of the invention, a method for applying energy to an object is presented, wherein energy is outputted to the object by energy emitting elements independently from each other. The energy emitting elements are preferentially located on an abutting surface, which abuts against a surface of the object during applying energy to the object.

In a further aspect of the invention, a computer program for applying energy to an object is presented, the computer program comprising program code means for causing a computer to carry out the steps of the described method, when the computer program is run on a computer controlling the described apparatus.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
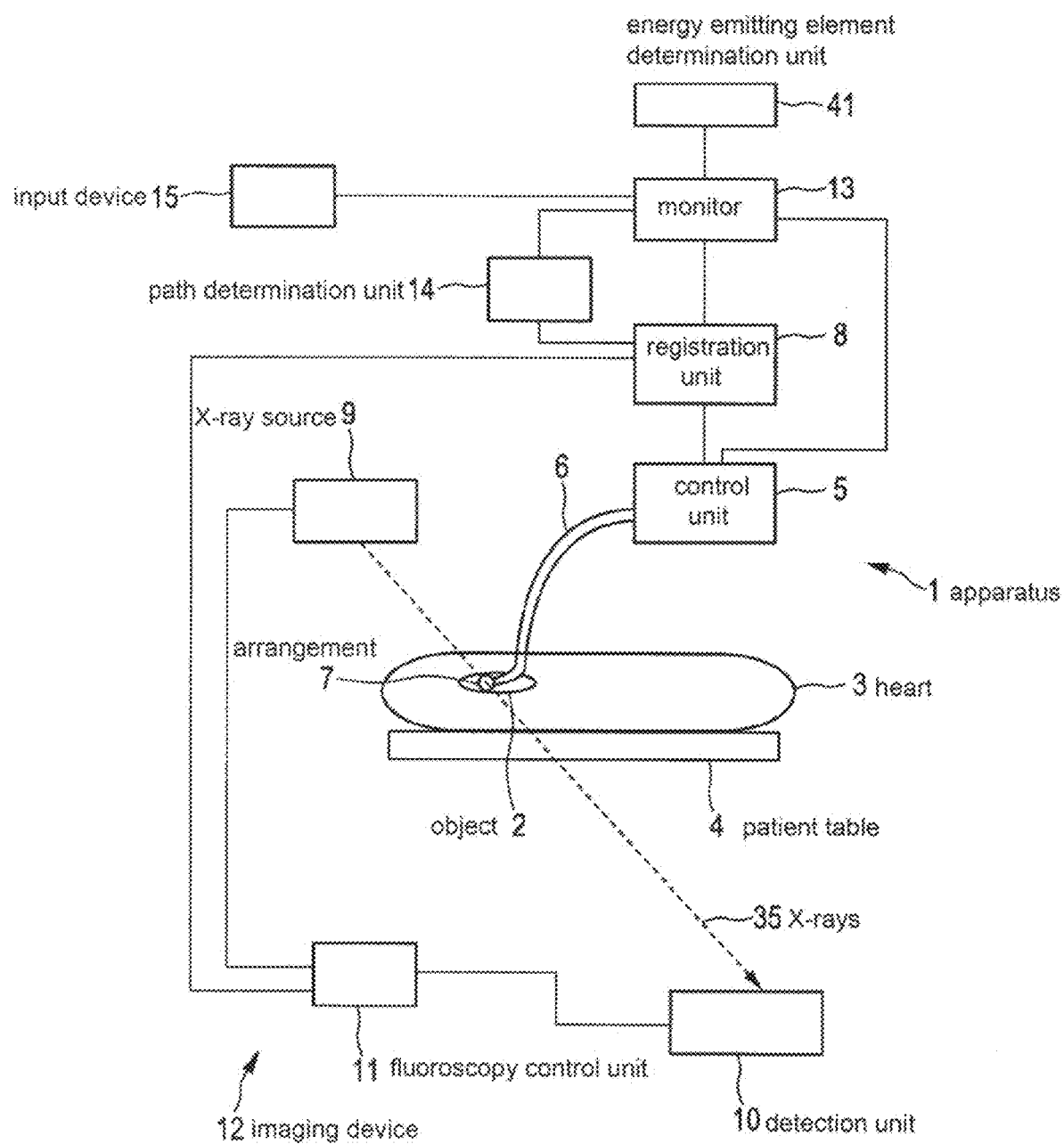
FIG. 1 shows schematically an embodiment for applying energy to an object in accordance with the invention.

FIG. 1 shows an apparatus 1 for applying energy to an object. The apparatus 1 comprises a catheter 6 and an arrangement 7 of energy emitting elements. The arrangement 7 of energy emitting elements is connected to a control unit 5 via the catheter 6. The catheter 6 with the arrangement 7 of energy emitting elements can be introduced into an object 2, which is, in this embodiment, a heart of a patient 3 located on a patient table 4.

During introduction of the arrangement 7 and the catheter 6 into the object 2 an imaging device 12, which is in this embodiment a fluoroscopy device, generates images of the object 2 and the arrangement 7. This imaging device 12 preferentially generates images of the object 2 and the arrangement 7, also if the arrangement 7 is already located within the object 2.

In other embodiments, the object can, for example, be another hollow organ of a patient or a technical object, in particular, a hollow technical object, whose inner surface has to be treated with energy.

The imaging device 12, i.e. in this embodiment the fluoroscopy device 12, comprises an X-ray source 9 and a detection unit 10, which are controlled by a fluoroscopy control unit 11. The fluoroscopy device 12 generates X-ray projection images of the object 2 and of the arrangement 7 in a known way. The X-rays of the X-ray source 9 are schematically indicated by the arrow 35.

In another embodiment, instead of a fluoroscopy device, another imaging device can be used for generating an image comprising the object 2 and the arrangement 7. For example, a magnetic resonance imaging device, a ultra sonic imaging device or a computed tomography imaging device can be used for generating an image of the object 2 and the arrangement 7.

Figure 2:
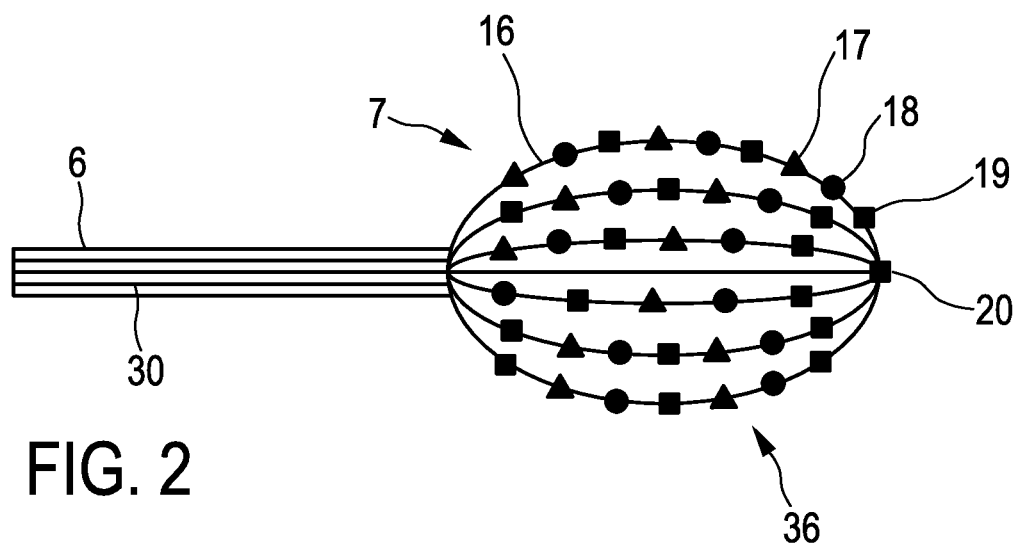
FIG. 2 shows schematically an arrangement of energy emitting elements comprising a basket in a first condition.

An embodiment of an arrangement 7 and an catheter 6 is schematically shown in more detail in FIG. 2. The arrangement 7 is changeable between a first condition, in which energy emitting elements 19 of the arrangement 7 are located on an abutting surface 36 abutting against a surface of the object, and a second condition, in which the arrangement 7 takes a smaller space, which allows to introduce the arrangement 7 into the object 2. In FIG. 2 the arrangement 7 is shown in its first condition. The arrangement 7 comprises a basket made of several splines 16, at which the energy emitting elements 19 (indicated by squares) and sensing elements 17, 18 (indicated by circles and triangles) are attached. The distribution of the energy emitting elements 19 and the sensing elements 17, 18 in FIG. 2 is only schematically and exemplarily and does not limit the invention to a certain distribution. Preferentially, the energy emitting elements 19 are evenly distributed along the splines 16 and along the abutting surface 36, and the sensing element 17, 18 are located as close as possible to the energy emitting elements 19.

In the first condition, which is shown in FIG. 2, the splines 16 of the basket form substantially an ellipsoid or spherical object. Thus, in the first condition, the abutting surface 36 is preferentially a surface of an ellipsoid or spherical object. For applying energy to the object 2, the abutting surface 36 abuts against a surface of the object 2 such that the positions of the energy emitting elements 19 and of the sensing elements 17, 18 remain unchanged relative to the surface of the object 2 during the application of energy to the object 2 and during sensing the surface of the object 2. This fixed positions of the energy emitting elements 19 and of the sensing sensors 17, 18 relative to the object surface are preferentially achieved by elastics properties of the splines 16 and, therefore, of the basket. This elasticity of the splines 16 results in an elastics force, which presses the energy emitting elements 19 and the sensing elements 17, 18 against the object surface. The elasticity of the splines 16 also allows conforming of the abutting surface 36 to the object surfaces and following a motion of the object 2, while the energy emitting elements 19 and the sensing elements 17, 18 are continuously in contact with the object surface, or, in other embodiments, the distance between the energy emitting elements and the sensing elements to the object surfaces remains continuously constant, even if the object 2 moves.

Figure 3:
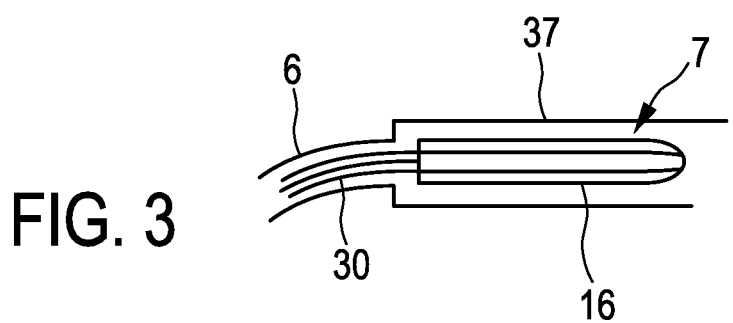
FIG. 3 shows schematically the arrangement of energy emitting elements in a second condition.

The splines 16 comprise wires made of nitinol. For unfolding the arrangement 7, i.e. for unfolding of the basket, the memory alloy of nitinol is used. The nitinol wires are pre-formed and elastic as a spring. In the second condition, which is schematically shown in FIG. 3 and in which the arrangement 7 takes a smaller space, the splines 16 of the basket are located within a catheter shaft 37, in particular, in a small pipe within the catheter shaft 37. For unfolding the arrangement 7, i.e. for changing from the second condition to the first condition, the splines 16 are moved out of the catheter shaft 37, wherein the arrangement 7 forms the abutting surface 36 because of the memory effect of the nitinol wires.

FIG. 3 is a schematic view only. For a clearer illustration of the second condition of the basket, less splines and no energy emitting and sensing elements are shown, although they are still present.

On the distal part of the abutting surface 36 an energy emitting element 20 is located, i.e. the energy emitting element 20 is located on the tip of the arrangement 7. This allows applying energy to certain locations of the object 2, if the splines 16 are at least almost completely located within the catheter shaft 37, wherein only a small part of the splines 16, i.e. at least only the emitting element 20, is located outside of the catheter shaft 37. Thus, energy can be applied to a certain location of the object 2, even if the arrangement 7 is in the second condition.

To each energy emitting element 19, 20 a line 30 for applying energy is connected. The energy emitting elements 19, 20 are connected to one or several energy sources via the lines 30 such that at least some of the energy emitting elements 19, 20 can apply energy to the object 2 independently from each other. It is preferred that the energy emitting elements 19, 20 are connected to one or several energy sources via the lines 30 such that each energy emitting element 19, 20 can be addressed separately, i.e. that each emitting element 19, 20 can apply energy to the object independently from a possible application of energy caused by the other energy emitting elements 19, 20.

The energy emitting elements 19, 20 are, in this embodiment, optical fiber diffusers, which are connected via the lines 30, which are in this embodiment optical fibers, to one or several light sources, which are preferentially lasers. In this embodiment, each optical fiber diffuser 19, 20 is connected to one or several separate laser devices via the optical fiber 30 to address each optical fiber diffuser 19, 20 separately. In other embodiments, in addition or alternatively, the emitting energy elements 19, 20 can be micro lenses or electrodes for applying electrical energy.

The optical fiber diffusers 19, 20 can be connected to one or several laser devices such that, after the laser beams of the laser devices have been divided, for example by beam splitters, each optical fibers diffuser is connected to an individual laser beam, wherein the intensity of each individual laser beam can be modified, in order to address each optical fiber diffuser 19, 20 separately. Alternatively, each optical fiber diffusers 19, 20 can be connected to an individual laser device such that to each optical fiber diffuser 19, 20 one of several laser devices is assigned.

The energy emitting elements 19, 20 and the sensing elements 17, 18 are attached to the nitinol wires, for example, by gluing.

Figure 4:
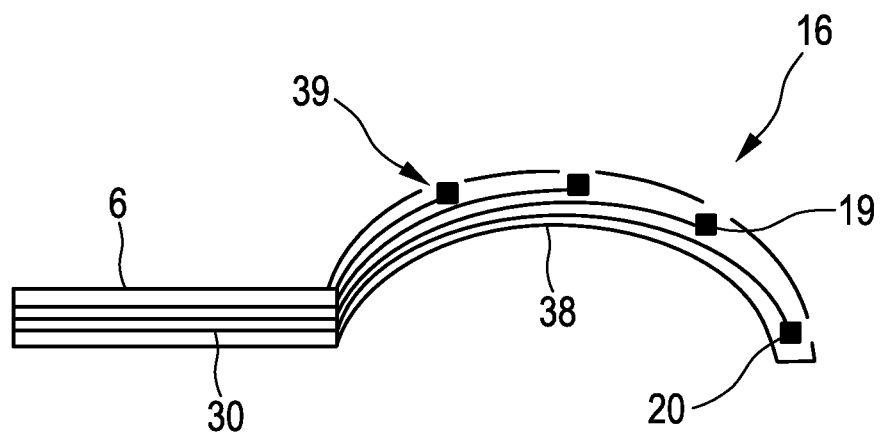
FIG. 4 shows schematically a spline of the arrangement of energy emitting elements.

Each spline is enclosed by an elastic casing, which is made of bio-compatible material. A part of a spline 16, which such an elastic casing 38, is schematically shown in FIG. 4. In FIG. 4 only some of the energy emitting elements 19, 20 are shown. Further energy emitting elements 19 and the sensing elements 17, 18 are also located within the casing 38, but these elements are not shown in FIG. 4. The casing 38 comprises optically transparent windows 39, which are located at the positions of the energy emitting elements 19, 20 for allowing the radiation to leave the casing 38. Alternatively, a casing can be used, which is completely optically transparent. In the latter case, additional optically transparent windows are not required.

The sensing elements 17, 18 are, in this embodiment, electrical sensors 17 and temperature sensors 18. The electrical sensors 17 measure the electrical potential of the object and the temperature sensors 18 measure the temperature of the object. These sensing elements 17, 18 are preferentially used for monitoring properties of the object, like the electrical potential or the temperature, during the application of the energy.

The temperature sensors 18 allow, for example, an electrical measurement of the temperature via thermocouples or a fiber-optical measurement of the temperature.

Since these temperature measurements and also the electrical sensing by the electrical sensors 17 do not interfere with the application of optical energy by the energy emitting elements 19, 20, the sensing of the object 2 and the application of energy can be performed simultaneously. This allows monitoring the properties of the objects, in particular, of the object surface, while energy is applied to the object. For example, if energy is applied for performing an ablation procedure, the progress of this procedure can monitored during the ablation procedure.

In another embodiment, a time-multiplex method can be used, which alternately applies energy and senses the object.

The sensor elements can also comprise spectroscopic sensors for sensing light reflected from the object surfaces. The reflected light is transmitted to a spectroscope via an optical fiber for a spectroscopic examination of the object.

The sensing elements 17, 18 are individually addressable. For example, electrical sensors, like electrical potential sensors or temperature sensors, are individually contacted by wires and optical sensors are individually contacted via optical fibers. This means, each sensing element is preferentially contacted via a separate line 30.

Figure 5:
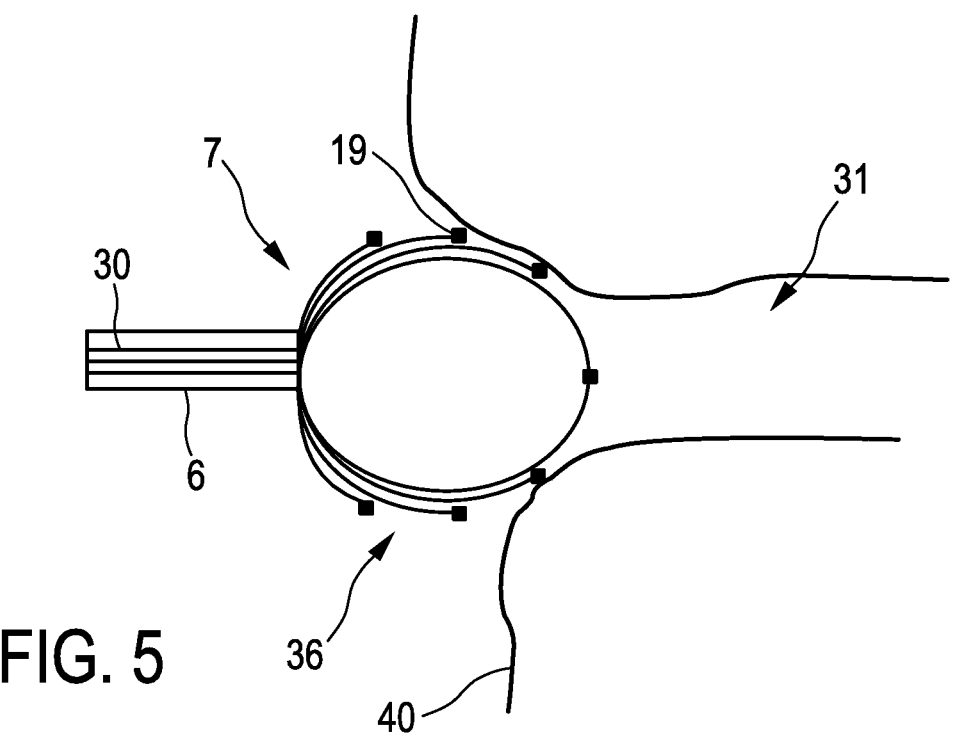
FIG. 5 shows schematically the arrangement of energy emitting elements in contact with a surface of an object.

FIG. 5 shows schematically an arrangement 7 located within a heart of a patient in a first condition, in which the abutting surface 36 abuts against the object surface 40 around an ostium of a pulmonary vein 31, i.e. in this embodiment a part of the abutting surface 36 abuts against the object surface 40. Energy emitting elements 19 can apply energy, in this embodiment light energy, to the object surface 40 independently from each other in order to denaturize heart tissue around the ostium or the pulmonary vein 31.

FIG. 5 shows schematically only two splines of the arrangement 7 without a casing and without sensing elements for illustration purposes. Nevertheless, also in the situation shown in FIG. 5, the arrangement 7 comprises different splines, wherein each spline includes several energy emitting elements and sensing elements preferentially enclosed within a casing, as described above and, for example, schematically shown in FIG. 2 and FIG. 4.

Figure 6:
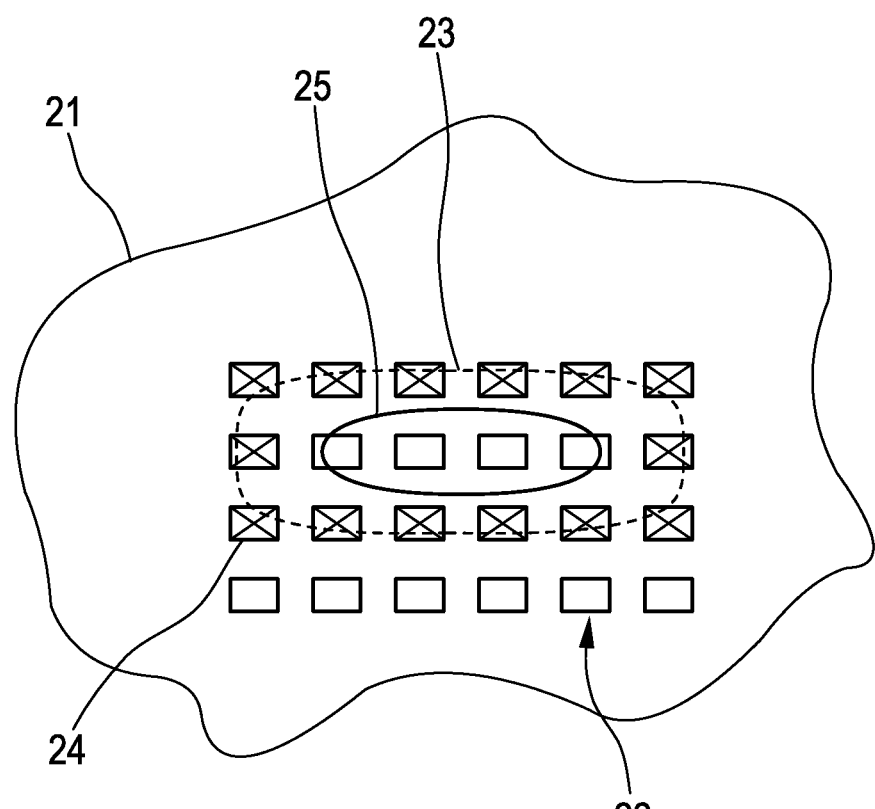
FIG. 6 shows schematically a model of an abutting surface of the arrangement of energy emitting elements located on a three-dimensional model of the object.

In this embodiment, the apparatus 1 for applying energy to an object is provided with a three-dimensional model of the object 2. This three-dimensional model can, for example, be generated by generating an image of the object 2 by an imaging device, like a computed tomography device, a magnetic resonance imaging device or a ultrasonic imaging device, by segmenting the object 2 and, for example, rendering of the segmented object 2. Furthermore, the apparatus 1 for applying energy to an object is further provided with a model of the abutting surface 36, which comprises, in this embodiment, the dimensions and the positions of the energy emitting elements 19, 20 on the abutting surface 36. A three-dimensional model 21 of the object 2 and a model 22 of the abutting surface 36 is schematically shown in FIG. 6. The model 22 of the abutting surface 36 is registered with the three-dimensional model 21 of the object by using the image generated by the fluoroscopy device 12. This registration is performed by a registration unit 8 of the apparatus 1.

The registration unit 8 is adapted for registering the three-dimensional model 21 of the object 2 with respect to the image generated by the imaging device 12, which is, in this embodiment, a two-dimensional projection image. For registering of the three-dimensional model of the object of the two-dimensional projection image known 2D-3D-registration methods can be used.

Furthermore, the registration unit 8 is adapted for registering the model 22 of the abutting surface 36 with respect to the image generated by the imaging device 12. Also for this registration, known 2D-3D-registration methods can be used. Since both models 21, 22 have been registered with respect to the two-dimensional projection image, these two models 21, 22 are registered with respect to each other.

The apparatus 1 for applying energy to an object further comprises a visualization device, which is, in this embodiment, a monitor 13, the visualization device is adapted for showing the three-dimensional model 21 of the object 2 and the model 22 of the abutting surface 36. The apparatus 1 for applying energy to an object further comprises an input device 15, like a mouse or a keyboard to allow a user to draw a path 23 on the three-dimensional model 21 of the object, along which energy should be applied to the object 2. Based on this path 23 an energy emitting element determination unit 41 determines energy emitting elements of the model 22 of the abutting surface 36 which are located on or as close as possible to this path 23. In FIG. 6 these determined energy emitting elements 24 are shown with crosses.

In the example shown in FIG. 6, the three-dimensional model 21 is a three-dimensional model of a heart showing an ostium 25 of a pulmonary vein. The heart tissue around the ostium 25 should be denaturized. Therefore, a user has inputted a path 23, which surrounds the ostium 25 of the pulmonary vein. The energy emitting elements 24, which are shown with a cross, are located on or close to the path 23, and during a following ablation procedure energy will be applied to the object 2 via the crossed energy emitting elements 24.

Other paths, along which energy should be applied to the object, can be provided in accordance with the invention. For example, for a linear ablation procedure, a open path, which is substantially linear and which connects two ostiums of pulmonary veins, can be used for applying energy along this path.

The energy emitting elements 24 are determined such that energy is applied to the object in a spatially continuous way, i.e. that energy is applied continuously along the respective path, without having gaps, at which energy has not been applied.

Optionally, the apparatus 1 for applying energy to an object further comprises a path determination unit 14, which automatically determines the path 23 on the three-dimensional model 21 of the object. In this case, the path determination unit 14 receives the three-dimensional model 21 of the object and/or sensing values of the sensing elements for determining the properties of the object, and the path determination unit 14 determines a path 23 from the model 21 and/or the determined properties of the object depending on the desired treatment of the object. For example, if the object is a heart and the path has to enclose the ostium of a pulmonary vein, which can be determined from the model 21 and/or the sensing values, for example, from an electrical potential image of the heart generated by using sensing electrodes, the path is determined such that it encloses, with a given distance to the edge of the ostium, the ostium of the pulmonary vein. The given distance can be predetermined by a user like a physician. The determined path is shown on the visualization device 13.

The input device 15 is adapted such that a user can modify the path 23 and/or at an additional path on the three-dimensional model 21 of the object. Furthermore, the input device 15 is adapted for modifying the determined emitting elements 24, which should apply energy. Furthermore, the apparatus 1 for applying energy to an object can be adapted for allowing a user to select the energy emitting elements 24, which should apply energy, directly with or without showing a path 23.

Figure 7:
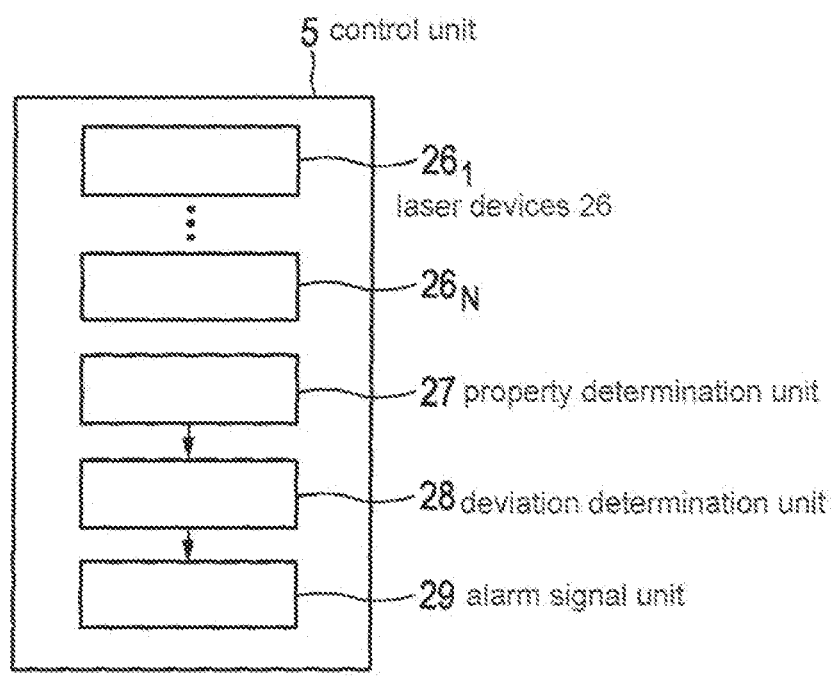
FIG. 7 shows a control unit for the apparatus for applying energy to applying energy to an object.

FIG. 7 shows schematically the control unit 5 of the apparatus 1 for applying energy to an object. In this embodiment, the control unit 5 comprises several light sources, in particular, laser devices $26_1 \ldots 26_N$, wherein the number N of these laser devices corresponds to the number of the separate energy emitting elements 19, 20 of the arrangement 7. Each laser device $26_1 \ldots 26_N$ is coupled to a separate energy emitting element 19, 20. The control unit 5 further comprises a property determination unit 27, which receives sensing values from the sensing elements 17, 18. The property determination unit 27 determines from these sensing values properties of the object 2, for example, the temperature or the electrical potential. These properties are transmitted to a deviation determination unit 28, which determines, whether the determined properties are within a given range of operation. If the determined properties are not within a given range operation, an alarm signal unit 29 outputs an acoustical or an optical signal indicating that the determined properties are out of range. Preferentially, the control unit 5 automatically reduces the intensity of the energy applied to the object, in particular, stops the application of energy, if the deviation determination unit 28 determines that at least one determined property of the object is out of range.

Figure 8:
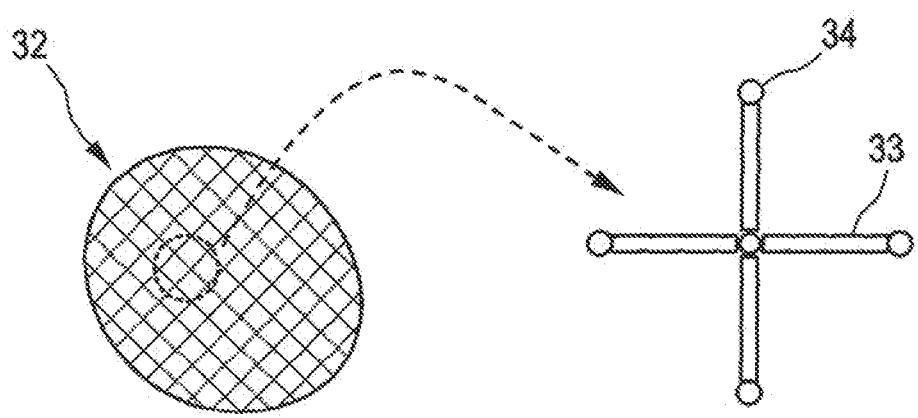
FIG. 8 shows schematically another embodiment of an arrangement of energy emitting elements in accordance with the invention.

FIG. 8 shows another embodiment of an arrangement 32 of energy emitting elements 33, which can be used together with the apparatus 1 shown in FIG. 2 instead of the arrangement 7. The arrangement 32 of energy emitting elements 33 is a mesh, wherein the grid points of the mesh form the sensing electrodes 34, and wherein the connecting parts between this grid points from the energy emitting elements 33. Some or all of the energy emitting elements 33 and of the sensing elements 34 are separately contacted, in order to address these elements independently from each other. The energy emitting elements 33 and the sensing element 34 are preferentially electrodes.

Although, the above-described arrangement 7 has been shown in FIG. 5 and in FIG. 6 as covering one ostium of a pulmonary vein, the ablation surface can also be dimensioned such that it can cover two ostia of pulmonary veins.

Figure 9:
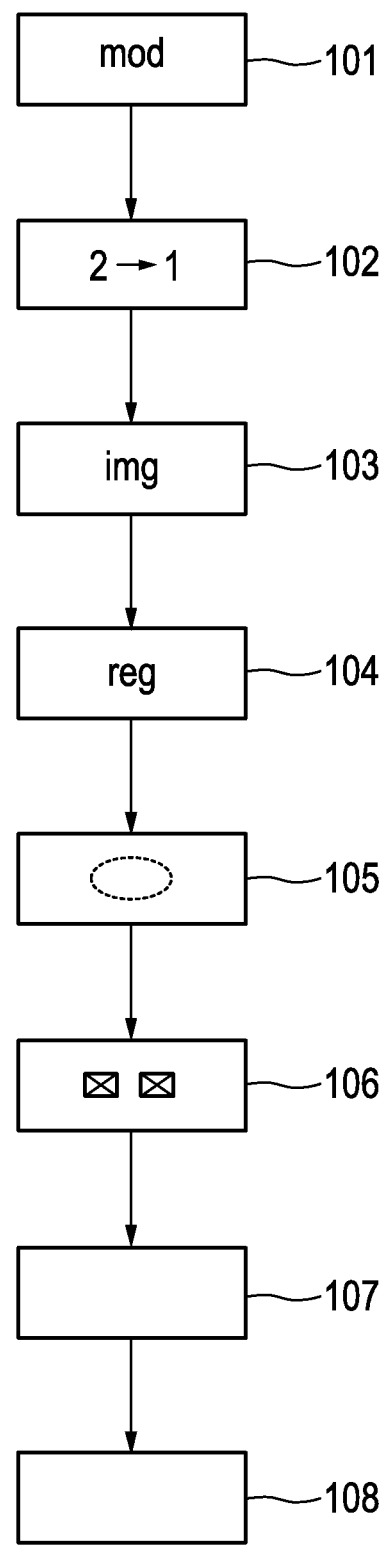
FIG. 9 shows a flow chart illustrating a method for applying energy to an object in accordance with the invention.

In the following a method for applying energy to an object in accordance with the invention will be described in more detail with reference to a flowchart shown in FIG. 9.

In step 101 a three-dimensional model 21 of the object 2 is provided to the apparatus 1 for applying energy to an object. Furthermore, a model 22 of the abutting surface 36 is provided to the apparatus 1 for applying energy to an object.

In step 102 the arrangement 7 of energy emitting elements, which is already located within the object 2, is unfolded, in order to transfer the arrangement 7 of energy emitting elements from the second condition to the first condition in which the abutting surface 36 abuts against an inner surface of the object 2 such that the position of the energy emitting elements with respect to the inner object surface remains constant during the following procedures.

In step 103 the imaging device 12 generates an image of the object 2 and of the abutting surface 36, and this image is transferred to the registration unit 8. The three-dimensional model 21 of the object 2 and the model 22 of the abutting surface 36 are registered relative to each other by using the image of the image generation device 12.

The registered models 21, 22 are visualized on the visualization device 13, and a path on the three-dimensional model 21 of the object 2 can be inputted to the apparatus 1 for applying energy to an object via the input device 15. As a default, the path determination unit 14 can determine a default path, which is also visualized on the visualization device 13 and which can be modified by a user using the input device 15.

Energy emitting elements 24 are determined in step 106, which are located on the given path or are located close to the given path, in order to map the given path to the abutting surface 36 as good as possible, by the energy emitting element determination unit 41. The position of these energy emitting elements, which should apply energy to the object, can be modified by a user via the input device 15.

In step 107 energy is applied to the object by the energy emitting elements, which have been determined and possibly modified by a user in step 106. While applying energy to the object, the properties of the object are monitored by the sensing elements 17, 18, the property determination unit 27 and the deviation determination unit 28.

The application of the energy is stopped in step 108, if a user inputs a corresponding stop signal into the apparatus 1 for applying energy to an object by the input device 15, if the property determination unit 27 determines properties of the object, which correspond to predetermined properties, which indicate the wanted modification of the object, or if the deviation determination unit 28 determines that at least one of the properties of the object are out of range.

The described method using the apparatus 1 for applying energy to an object allows positioning the arrangement 7 of energy emitting elements roughly relative to the object, because the exact path, along which energy has to be applied to the object, is not determined by the positioning of the ablation surface 36, but by the determination and possibly modification of the energy emitting elements in step 106. Therefore, a time consuming positioning of the energy emitting elements can be omitted.

The three-dimensional model of the object, in particular, of a heart can be a purely anatomical model or an electro-anatomical model using the electrical potentials measured by the sensing electrodes.

The energy of the energy emitting elements can be applied concurrently or automatically in time coordinated way. Furthermore, the successful application of energy, in particular, the successful ablation, i.e. the electrical isolation of heart tissue, can be validated by the sensing elements in the arrangement 7 of energy emitting elements.

The sensing elements of the arrangement 7 of energy emitting elements provide an electro-anatomical mapping of the object tissue, in particular of the heart tissue, which can be used for detecting relevant structures like the ostium of the pulmonary veins. This electro-anatomical mapping can also be used to determine a model of the object and to register the model of the object with a model of the abutting surface of the arrangement of emitting elements.

In step 107 the energy applied to the object can be controlled such that too high temperatures in the object, in particular, in the heart tissue, are avoided. Thus, if the temperature becomes too high, the control unit 5 reduces preferentially the energy applied to the object. In the case of heart tissue, a temperature above 80° C. is generally too high.

The invention can be used for mapping the four chambers of a heart, for ablation in four chambers of a heart, for an electrical isolation of pulmonary veins and for a substrate modification.

The light sources $26_1 \ldots 26_N$ are preferentially infrared laser devices with a wavelength in the range of 960 nm to 1100 nm.

Furthermore, the position of a structure of interest, for example of the ostium of the pulmonary vein, can be located by sensing the electrical potentials at the object surface by the sensing elements. The location of the structure of interest can be mapped into a geometrical map, and this geometrical information of the location and the size of the ostium of a pulmonary vein can be mapped into a three-dimensional model of the object, in particular, of a heart of a patient. The size and the position of the ostium will be shown on the three-dimensional model of the object by the visualization device 13 for allowing a user to input a path, along which energy has to be applied, or allow to automatically determine such a path.

Although, a fluoroscopy device has been described above as the imaging device, another imaging device, for example, a magnetic resonance device or an ultrasonic imaging device can be used in order to visualize the object and the arrangement of energy emitting elements particularly in real time.

The apparatus 1 for applying energy to an object can be used, for example, for circumferential ablation linear, and/or segmental ablation and/or a single point ablation.

While the invention has been illustrated and described in detail in the drawings and foregoing description such illustration and description are to be considered illustrative or exemplarily and not restrictive. The invention is not limited to the disclosed embodiments.

Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for applying energy to an object, wherein the apparatus comprises:
   an arrangement including energy emitting elements configured to output energy to the object and sensing elements, wherein at least some of the energy emitting elements are configured to emit energy to the object independently from each other, wherein the arrangement comprises an abutting surface during application of the energy to the object, wherein the energy emitting elements and the sensing elements are located on the abutting surface at different locations and wherein the abutting surface is abutable against an object surface of the object;
   a path determination unit configured to automatically determine a path from measured properties of the object sensed by the sensing elements;
   a model generation unit configured to generate an object model representing the object for display of the object model including display of the path on the object model for applying the energy to the object along the path; and
   a control unit configured to select a portion of the energy emitting elements in response to the selected portion of the energy emitting elements being on the path and to automatically activate the selected portion of the energy emitting elements and apply the energy to the object from the selected portion of the energy emitting elements that are on the path.

2. The apparatus as claimed in claim 1,
   wherein the abutting surface is elastic for adapting to the object surface.

3. The apparatus as claimed in claim 1,
   wherein the arrangement is changeable between a first condition, in which the arrangement is expanded to a first size, and a second condition, in which the arrangement has a smaller size than the first size, and wherein at least one of the energy emitting elements is configured to apply the energy to the object when the arrangement is in the first condition and the second condition.

4. The apparatus as claimed in claim 3,
   wherein the arrangement is unfoldable to the first condition and foldable to the second condition.

5. The apparatus as claimed in claim 1,
   wherein the apparatus comprises a catheter coupled to the arrangement, wherein a location of the arrangement most distal to the catheter comprises at least one of the energy emitting elements.

6. The apparatus as claimed in claim 1,
   wherein the energy emitting elements are adapted for outputting light energy.

7. The apparatus as claimed in claim 1,
   wherein the sensing elements are configured to provide sensing values to the control unit, wherein the control unit is configured to notice whether the sensing values are outside of a predetermined range of operation.

8. The apparatus as claimed in claim 1, further comprising a registration unit configured to register the object model with a model of the abutting surface, the control unit being further configured to activate the selected energy emitting elements of the registered abutting surface which are arranged along the path, to apply the energy to the object, and the apparatus being provided with a model of the abutting surface representing the abutting surface, wherein the apparatus comprises an imaging device configured to generate an image of the object and of the abutting surface, wherein the registration unit is further configured to register the object model with the abutting surface by registering the object model and the model of the abutting surface with the generated image of the object and of the abutting surface generated by the imaging device.

9. The apparatus of claim 1, wherein the sensing elements are configured to sense a property of the object surface during the application of the energy from the selected energy emitting elements that are activated by the control unit such that the energy is applied and the property of the object is sensed simultaneously.

10. The apparatus of claim 1, further comprising an input device for at least one of modifying the automatically determined path and inputting a further path.

11. The apparatus of claim 1, further comprising an imaging system configured to provide an image of the object for registration of the image with the object model.

12. The apparatus of claim 1, wherein the control unit is further configured to not activate a remaining portion of the energy emitting elements which are not along the path.

13. The apparatus of claim 1, wherein the energy emitting elements comprise optical elements configured to output light energy.

14. The apparatus of claim 1, wherein the sensing elements comprise a first sensing element and a second sensing element that are located between at least two energy emitting elements of the selected portion, and wherein the first sensing element comprises a voltage sensor and the second sensing element comprises a temperature sensor.

15. The apparatus of claim 1, wherein the abutting surface includes splines, and wherein the energy emitting elements and the sensing elements are attached to the splines.

16. The apparatus of claim 15, wherein the splines comprise memory material having a pre-formed and elastic shape, wherein the splines are configured to fold into a smaller shape smaller than the pre-formed and elastic shape when the splines are located within a catheter shaft, and wherein the splines are configured to unfold into the pre-formed and elastic shape when the splines are moved out of the catheter shaft.

17. The apparatus of claim 16, wherein the splines have elastics properties resulting in an elastics force that presses the energy emitting elements and the sensing elements against the object surface such that positions of the energy emitting elements and of the sensing elements remain unchanged relative to the object surface during the application of the energy to the object by the energy emitting elements and during sensing by the sensing elements.

18. The apparatus of claim 1, wherein the sensing elements comprise a first sensing element and a second sensing element that are located between at least two energy emitting elements of the selected portion and are configured to sense different properties of the object surface.

19. The apparatus of claim 1, wherein the abutting surface includes splines, wherein a set of the energy emitting elements and the sensing elements are attached to the splines, and wherein the set includes a repeating sequence of a first enemy emitting element, a first sensing element, and a second sensing element.

20. The apparatus of claim 1, wherein the control unit is configured to concurrently activate the selected portion of the selected energy emitting elements.

21. A method for applying energy to an object comprising the act of:
   providing an arrangement including energy emitting elements for outputting energy to the object and sensing element, wherein at least some of the energy emitting elements are configured to emit energy to the object independently from each other, wherein the arrangement comprises an abutting surface during application of the energy to the object, wherein the energy emitting elements are located on the abutting surface at different locations and wherein the abutting surface is abutable against an object surface of the object;

automatically determining a path from measured properties of the object sensed by the sensing elements;

generating an object model representing the object;

displaying the object model including displaying of the path on the object model for applying the energy to the object along the path; and in response to a portion of the energy emitting elements being on the path, selecting the portion of the energy emitting elements for automatic activation of the selected portion of the selected energy emitting elements to apply energy to the object from the selected portion of the energy emitting elements that are on the path.

22. The method of claim 21, wherein the selecting act selects the portion of the energy emitting elements for the activation while not activating a remaining portion of the energy emitting elements which is not along the path.

23. The method of claim 21, wherein the energy emitting elements comprise optical elements configured to output light energy, and wherein the sensing elements comprise first and second sensing elements that are configured to sense different properties of the object surface.

24. The method of claim 23, wherein the first and second sensing elements comprise a voltage sensor and a temperature sensor.

25. The method of claim 21, further comprising the acts of:

registering the object model with a model of the abutting surface; and activating the selected energy emitting elements of the registered abutting surface which are arranged along the path, to apply energy to the object.

26. The method of claim 21, wherein the abutting surface includes splines, and wherein the energy emitting elements and the sensing elements are attached to the splines.

27. The method of claim 26, wherein the splines comprise memory material having a pre-formed and elastic shape, wherein the splines are configured to fold into a smaller shape smaller than the pre-formed and elastic shape when the splines are located within a catheter shaft, and wherein the splines are configured to unfold into the pre-formed and elastic shape when the splines are moved out of the catheter shaft.

28. The method of claim 27, wherein the splines have elastics properties resulting in an elastics force that presses the energy emitting elements and the sensing elements against the object surface such that positions of the energy emitting elements and of the sensing elements remain unchanged relative to the object surface during the application of the energy to the object by the energy emitting elements and during sensing by the sensing elements.

29. A non-transitory computer eadable medium embodying a computer program for applying energy to an object, the computer program comprising instructions which, when executed by a processor, configure the processor to perform the acts of:

controlling an arrangement including energy emitting elements for outputting energy to the object and sensing element for sensing the object, wherein at least some of the energy emitting elements are configured to emit energy to the object independently from each other, wherein the arrangement comprises an abutting surface during application of the energy to the object, wherein the energy emitting elements are located on the abutting surface at different locations and wherein the abutting surface is abutable against an object surface of the object;

automatically determining a path from measured properties of the object sensed by the sensing elements;

generating an object model representing the object;

displaying the object model including displaying of a path on the object model for applying the energy to the object along the path; and in response to a portion of the energy emitting elements being on the path, selecting a portion of the energy emitting elements for automatic activation of the selected portion of the selected energy emitting elements to apply the energy to the object from the selected portion of the energy emitting elements that are on the path.

30. The non-transitory computer readable medium of claim 29, wherein the energy emitting elements comprise optical elements configured to output light energy, and wherein the sensing elements comprise first and second sensing elements that are configured to sense different properties of the object surface.

31. The non-transitory computer readable medium of claim 30, wherein the first and second sensing elements comprise a voltage sensor and a temperature sensor.

32. The non-transitory computer readable medium of claim 29, wherein the instructions which, when executed by a processor, further configure the processor to perform the acts of:

registering the object model with a model of the abutting surface; and activating the selected energy emitting elements of the registered abutting surface which are arranged along the path, to apply energy to the object.

33. The non-transitory computer readable medium of claim 29, wherein the abutting surface includes splines, and wherein the energy emitting elements and the sensing elements are attached to the splines.

34. The non-transitory computer readable medium of claim 33, wherein the splines comprise memory material having a pre-formed and elastic shape, wherein the splines are configured to fold into a smaller shape smaller than the pre-formed and elastic shape when the splines are located within a catheter shaft, and wherein the splines are configured to unfold into the pre-formed and elastic shape when the splines are moved out of the catheter shaft.

35. The non-transitory computer readable medium of claim 34, wherein the splines have elastics properties resulting in an elastics force that presses the energy emitting elements and the sensing elements against the object surface such that positions of the energy emitting elements and of the sensing elements remain unchanged relative to the object surface during the application of the energy to the object by the energy emitting elements and during sensing by the sensing elements.

* * * * *